United States Patent
Wang et al.

(10) Patent No.: US 10,653,803 B2
(45) Date of Patent: May 19, 2020

(54) CELLULAR MICROMOTORS AND USES THEREOF

(71) Applicant: The Regents of the University of California, Oakland, CA (US)

(72) Inventors: Joseph Wang, San Diego, CA (US); Liangfang Zhang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 412 days.

(21) Appl. No.: 15/356,977

(22) Filed: Nov. 21, 2016

(65) Prior Publication Data

US 2017/0143830 A1     May 25, 2017

Related U.S. Application Data

(60) Provisional application No. 62/257,882, filed on Nov. 20, 2015.

(51) Int. Cl.

| | |
|---|---|
| *A61K 41/00* | (2020.01) |
| *A61K 49/00* | (2006.01) |
| *A61K 35/18* | (2015.01) |
| *A61K 9/50* | (2006.01) |
| *A61K 47/69* | (2017.01) |
| *A61K 9/51* | (2006.01) |
| *A61K 9/00* | (2006.01) |
| *A61K 35/12* | (2015.01) |

(52) U.S. Cl.
CPC ........ *A61K 49/0097* (2013.01); *A61K 9/0009* (2013.01); *A61K 9/5094* (2013.01); *A61K 9/5115* (2013.01); *A61K 35/18* (2013.01); *A61K 41/00* (2013.01); *A61K 47/6901* (2017.08); *A61K 49/0067* (2013.01); *A61K 2035/124* (2013.01)

(58) Field of Classification Search
CPC .. A61K 49/0097; A61K 9/0009; A61K 41/00; A61K 9/5094; A61K 35/18; A61K 2035/124; A61K 49/0067; A61K 47/6901; A61K 9/5115
See application file for complete search history.

(56) References Cited

U.S. PATENT DOCUMENTS

2008/0154128 A1* 6/2008 Milner ...................... 600/427

OTHER PUBLICATIONS

Cinti et al., Newly engineered magnetic erythrocytes for sustained and targeted delivery of anti-cancer therapeutic compounds. PLoS One, vol. 6, No. 2 Feb. 23, 2011) e17132. (Year: 2011).*
Nano-screenMAG. Datasheet [online].Chemicell, 2011 [retrieved on Oct. 4, 2018]. Retrieved from the Internet: <URL: http://www.chemicell.com/products/magneticfluorescent/index.html>. (Year: 2011).*
Wu et al., Turning erythrocytes into functional micromotors. ACS Nano, vol. 8, No. 12 (Nov. 21, 2014) pp. 12041-12048. (Year: 2014).*
Antonelli et al., Encapsulation of superparamagnetic nanoparticles into red blood cells as new carriers of MRI contrast agents. Nanomedicine, vol. 6, No. 2 (2011) pp. 211-223 (Year: 2011).*
Antonelli et al., Red blood cells as carriers or iron oxide-based contrast agents for diagnostic applications. Journal of Biomedical Nanotechnology, vol. 10 (2014) pp. 1732-1750 (Year: 2014).*
Malvern—"Dynamic light scattering—Common terms defined", an Inform White Paper, 2011 published by Malvern Instruments Ltd., MRK1764-01, total pp. 1-6. (Year: 2011).*
Dreyfus, R., et al. "Microscopic Artificial Swimmers," Nature 2005, 437, 862-865.
Paxton, W. F., et al. "Catalytic Nanomotors: Autonomous Movement of Striped Nanorods," J. Am. Chem. Soc. 2004, 126, 13424-13431.
Wilson, D. A., et al. "Autonomous Movement of Platinum-Loaded Stomatocytes," Nat. Chem. 2012, 4, 268-274.
Weiss, P. S., et al. "Nanotechnology: A Molecular Four-Wheel Drive," Nature 2011, 479, 187-188.
Mei Y. F., et al. "Rolled-up Nanotech on Polymers: From Basic Perception to Self-Propelled Catalytic Microengines," Chem. Soc. Rev. 2011, 40, 2109-2119.
Loget, G., et al. "Electric Field-induced Chemical Locomotion of Conducting Objects," Nat. Commun. 2011, 2, 535.
Van Rhee, P. G., et al. "Polymersome Magneto-Valves for Reversible Capture and Release of Nanoparticles," Nat. Commun. 2014, 5.
Li, J., et al. "Nanomotor Lithography," Nat. Commun. 2014, 5.
Wu, J., et al. "Motion-Based DNA Detection Using Catalytic Nanomotors," Nat. Commun. 2010, 1, 36.
Sengupta, S., et al. "Self-Powered Enzyme Micropumps," Nat. Chem. 2014, 6, 415-422.
Ikezoe, Y., et al. "Autonomous Motors of a Metal-Organic Framework Powered by Reorganization of Self-Assembled Peptides at Interfaces," Nat. Mater. 2012, 11, 1081-1085.
Solovev A. A., et al. "Magnetic Control of Tubular Catalytic Microbots for the Transport, Assembly, and Delivery of Microobjects," Adv. Funct. Mater. 2010, 20, 2430-2435.
Guix, M., et al. "Nano/Micromotors in (Bio)Chemical Science Applications," Chem. Rev. 2014, 114, 6285-6322.
Ismagilov, R. F., et al. "Autonomous Movement and Self-Assembly," Angew. Chem., Int. Ed. 2002, 114, 652-654.
Wang, W., et al. "Small Power: Autonomous Nano- and Micromotors Propelled by Self-Generated Gradients," Nano Today 2013, 8, 531-554.
Tottori, S., et al. "Assembly, Disassembly, and Anomalous Propulsion of Microscopic Helices," Nano Lett.2013, 13, 4263-4268.
Wang, W., et al. "Autonomous Motion of Metallic Microrods Propelled by Ultrasound," ACS Nano 2012, 6, 6122-6132.

(Continued)

*Primary Examiner* — Satyendra K Singh
(74) *Attorney, Agent, or Firm* — Eversheds Sutherland (US) LLP

(57) ABSTRACT

Living cells, such as red blood cells (RBCs) modified with functional micromotors with the aid of ultrasound propulsion and magnetic guidance. Iron oxide nanoparticles are loaded into the RBCs, where their asymmetric distribution within the cells results in a net magnetization, thus enabling magnetic alignment and guidance under acoustic propulsion. The RBC motors display efficient guided and prolonged propulsion in various biological fluids, including undiluted whole blood.

12 Claims, 8 Drawing Sheets

(56) References Cited

OTHER PUBLICATIONS

Fischer., et al. "Magnetically actuated propulsion at low Reynolds numbers: towards nanoscale control,". Nanoscale 3, 557-563 (2011).
Schamel, D., et al. "Nanopropellers and Their Actuation in Complex Viscoelastic Media," ACS Nano 2014, 8, 8794-8801.
Zhang, L., et al. "Nanoparticle-Assisted Surface Immobilization of Phospholipid Liposomes," J. Am. Chem. Soc. 2006, 128, 9026-9027.
Zhang, L., et al. "Electrostatic Stitching in Gel-Phase Supported Phospholipid Bilayers," J. Phys. Chem. B 2005, 110, 33-35.
Love, K. T. et al. "Lipid-Like Materials for Low-Dose, in Vivo Gene Silencing," Proc. Natl. Acad. Sci. U.S.A. 2010, 107, 1864-1869.
Celiz, A. D., et al. "Materials for Stem Cell Factories of the Future," Nat. Mater. 2014, 13, 570-579.
Yang, F., et al. "Genetic Engineering of Human Stem Cells for Enhanced Angiogenesis Using Biodegradable Polymeric Nanoparticles," Proc. Natl. Acad. Sci. U.S.A. 2010, 107, 3317-3322.
Hu, C. M., et al. "Nanoparticle-Detained Toxins for Safe and Effective Vaccination," Nat. Nanotech. 2013, 8, 933-938.
Zhang, K., et al. "Ophthalmic Drug Discovery: Novel Targets and Mechanisms for Retinal Diseases and Glaucoma," Nat. Rev. Drug Discov. 2012, 11, 541-559.
Pierigè, F., et al. "Cell-Based Drug Delivery," Adv. Drug Deliv. Rev. 2008, 60, 286-295.
Brähler, M., et al. "Magnetite-Loaded Carrier Erythrocytes as Contrast Agents for Magnetic Resonance Imaging," Nano Lett. 2006, 6, 2505-2509.
Lee, J., et al. "Cytoprotective Silica Coating of Individual Mammalian Cells through Bioinspired Silicification," Angew. Chem., Int. Ed. 2014, 53, 8056-8059.
Muzykantov, V. R., et al. "Drug Delivery by Red Blood Cells: Vascular Carriers Designed by Mother Nature," Expert Opin. Drug Deliv. 2010, 7, 403-427.
Yoo, J. W., et al. "Bio-Inspired, Bioengineered and Biomimetic Drug Delivery Carriers," Nat. Rev. Drug Discov. 2011, 10, 521-535.
Ding, X., et al. "On-Chip Manipulation of Single Microparticles, Cells, and Organisms Using Surface Acoustic Waves," Proc. Natl. Acad. Sci. U.S.A. 2012, 109, 11105-11109.
Venugopalan, P. L., "Conformal Cytocompatible Ferrite Coatings Facilitate the Realization of a Nanovoyager in Human Blood," Nano Lett. 2014, 14, 1968-1975.
Kolesnikova, T. A., et al. "Red Blood Cells and Polyelectrolyte Multilayer Capsules: Natural Carriers versus Polymer-Based Drug Delivery Vehicles," Expert Opin. Drug Deliv. 2013, 10, 47-58.
Delcea, M., et al. "Nanoplasmonics for Dual-Molecule Release through Nanopores in the Membrane of Red Blood Cells," ACS Nano 2012, 6, 4169-4180.
Hu, C. M. J., et al. "Erythrocyte Membrane-Camouflaged Polymeric Nanoparticles as a Biomimetic Delivery Platform," Proc. Natl. Acad. Sci. U.S.A. 2011, 108, 10980-10985.
Wang, C., et al. "Multifunctional Theranostic Red Blood Cells for Magnetic-Field-Enhanced in Vivo Combination Therapy of Cancer," Adv. Mater 2014, 26, 4794-4802.
Z. Wu., et al. "Turning Erythrocytes into Functional Micromotors," ACS Nano, 2014, 8, 12041.
E. Chambers., et al. "Long Circulating Nanoparticles via Adhesion on Red Blood Cells: Mechanism and Extended Circulation," Exp. Biol. Med., 2007, 232, 958.
K. J. Rao, et al. "A Force to Be Reckoned With: A Review of Synthetic Microswimmers Powered by Ultrasound," Small, 2015, 11, 2836-2846.

* cited by examiner

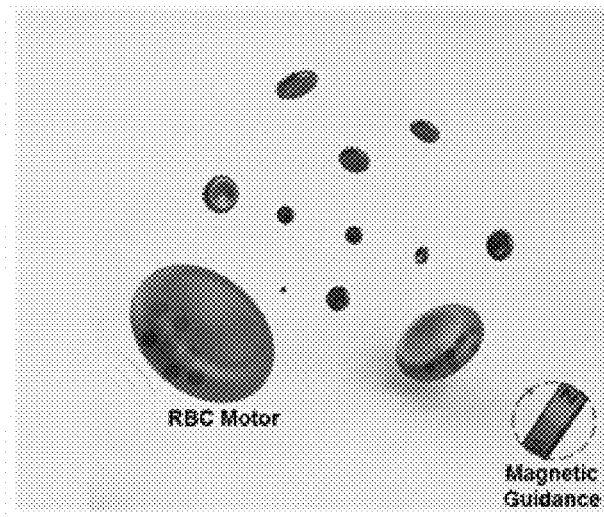
FIGURE 1A
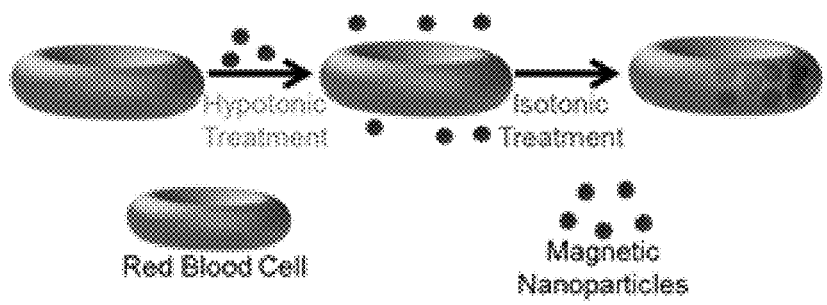
FIGURE 1B
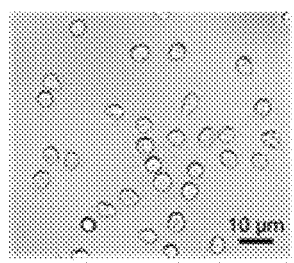 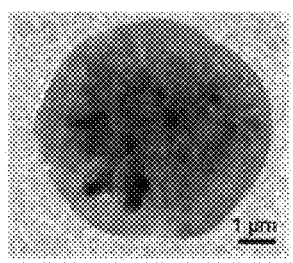
FIGURE 1C  FIGURE 1D

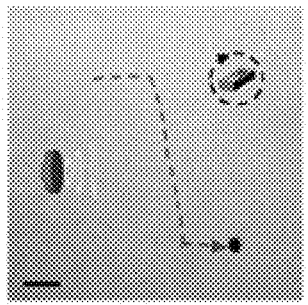 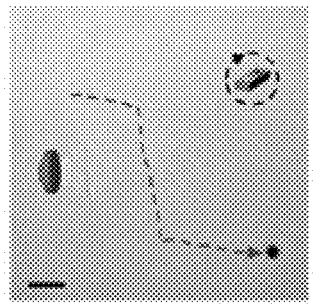 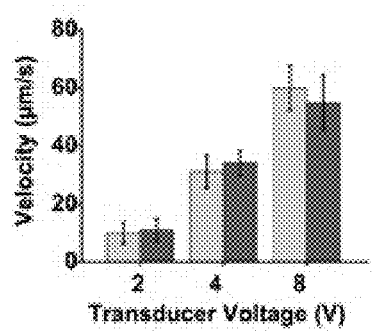
FIGURE 9A    FIGURE 9B    FIGURE 9C
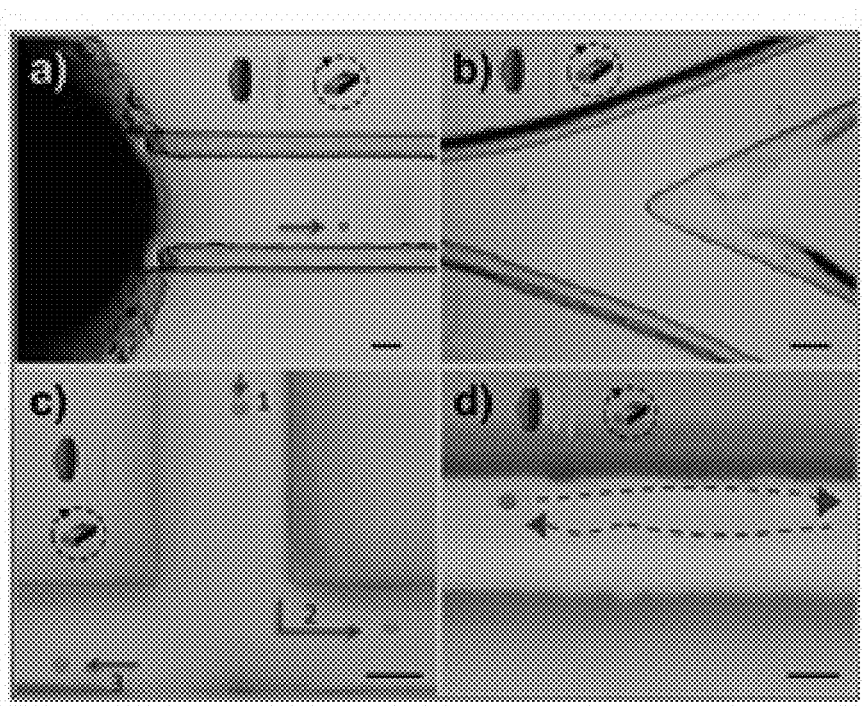
FIGURES 10A-10D

CELLULAR MICROMOTORS AND USES THEREOF

CROSS REFERENCES TO RELATED APPLICATIONS

This application claims priority to U.S. Provisional Application No. 62/257,882, filed Nov. 20, 2015, the entire contents of which are incorporated by reference herewith.

STATEMENT REGARDING FEDERALLY SPONSORED RESEARCH

This invention was made with government support under HDTRA1-13-1-0002 and HDTRA1-14-1-0064 awarded by the National Institutes of Health. The government has certain rights in the invention.

BACKGROUND

The development of nano/micromotors is a research area of intense activity due to numerous potential applications.[1-8] While considerable attention has been given to catalytic motors that exhibit self-propulsion in the presence of a hydrogen peroxide fuel, many practical applications would require elimination of the need of chemical fuel.[9-15] Several groups have thus explored fuel-free propulsion mechanisms based on externally applied magnetic or ultrasound fields.[16-20] The increased capabilities and sophistication of these tiny fuel-free motors hold considerable promise for directed drug delivery, biopsy, cleaning clogged arteries, precision nanosurgery, and localized diagnosis in hard-to-reach places, for example. To fulfill these exciting potential applications, particular attention is drawn to the biocompatibility of the motors in biological environments and to their performance in undiluted biological media. The metallic or polymeric components of common artificial nano/micromotors are facing destructive immune attack once entering into the bloodstream due to the foreign nature of these materials.

Natural cells and their derivatives are highly optimized by nature for their unique in vivo functions and possess attractive features desired for systemic cargo delivery.[21-23] As a result, various types of cells, such as red blood cells (RBCs, also referred to as erythrocytes), white blood cells, macrophages, engineered stem cells and so on, have been employed to carry and deliver therapeutic or imaging agents.[24,25] The intrinsic properties of these natural carriers have opened the door to creative cargo delivery strategies and novel biomaterials development. Among these cell-based carriers, RBCs are of particular interest owing to their vast availability, unique mechanical attribute, surface immunosuppressive property, and versatile cargo-carrying capability.[26-28] As such, numerous RBCs based or inspired delivery systems have been recently developed for cargo delivery, relying on the prolonged transport property of RBCs in the bloodstream.[29-32] However, there are no reports on how to bestow active propulsion force upon the passively moving RBCs, and thus to utilize the cells as a powerful autonomous micromotor.

Several groups have demonstrated the capability of synthetic micro/nanoscale motors for guided transport of drug-loaded nanoparticles and capture and transport of cells. However, the ability to transport diagnostic imaging agents and therapeutic drugs at the same time within a single powered motor, without affecting the propulsion and direction of the motor, has not yet been demonstrated. Such multicargo-loaded motors would provide an attractive delivery vehicle for the concurrent imaging and treatment of diseases.

SUMMARY OF THE INVENTION

The invention provides in one embodiment, an ultrasound-powered, magnetically-switchable RBC-based micromotor (denoted RBC motor). An ultrasound field can trigger the propulsion of microscale objects, and that movement is driven by the interaction between the objects and the distribution of acoustic forces within the field. The RBC motors can be prepared by loading iron-oxide nanoparticles into RBCs. The propulsion of the RBC motor can be attributed to the asymmetric distribution of iron oxide nanoparticles within the cell, which is useful for ultrasound-powered motion. The RBC motor can be propelled by the pressure gradient generated by the ultrasound waves due to the inherent asymmetric geometry of the RBC as well as the asymmetric distribution of magnetic particles inside the RBCs. The latter also provides a net magnetization that enables magnetic alignment and guidance under acoustic propulsion.

The magnetic guidance (orientation) of these RBC motors can be switched 'On' and 'Off' by applying an external magnetic field. The resulting RBC motors possess highly efficient, ultrasound-powered, magnetically-guided propulsion. The invention provides the efficient prolonged movement that the RBC motors display in the bloodstream over an extended period of time with no apparent biofouling effects. The RBC membrane serves as an intrinsic shield to protect the magnetic nanoparticles from etching by co-existing ions (e.g., chlorides, phosphates) in the blood, hence obviating the need for commonly used protective coatings. Moreover, one of the advantages of the inventive micromotors for biomedical applications is biocompatibility, or the ability of the motors to prevent detection and uptake by immune cells such as macrophages. Due to their inherent biomimetic properties, the new RBC motors are not susceptible to uptake by macrophages, displaying remarkable biocompatibility essential for practical biomedical uses.

In embodiments, the invention provides an imaging agent (CdTe quantum dot, QD) and an anti-cancer drug (doxorubicin, DOX) within an RBC micromotor to provide the coupling of both diagnostic and therapeutic modalities in a single vehicle.

BRIEF DESCRIPTION OF THE DRAWINGS

FIGS. 1A-1D illustrate red blood cells (RBC) motors of an embodiment of the invention. FIG. 1A is a schematic illustration of magnetically-guided, ultrasound-propelled RBC micromotors in whole blood. FIG. 1B shows the preparation of the RBC motors: magnetic nanoparticles are loaded into regular RBCs by using a hypotonic dilution encapsulation method. FIG. 1C is an optical and FIG. 1D transmission electron microscopy images of the RBC motors.

FIG. 2B under magnetic field alone; FIG. 2C under magnetic field in the presence of regular (non-magnetic) RBCs; FIG. 2D under ultrasound field alone; FIG. 2E under both magnetic and ultrasound fields; and FIG. 2F under both magnetic and ultrasound fields in the presence of regular RBCs (non-magnetic). Scale bars, 20 μm.

FIG. 3A is a schematic illustration showing the projected motion trajectory of the RBC motor under ultrasound field with On-Off switchable magnetic field. FIG. 3B is an actual time-lapse image, illustrating the movement of the RBC motor under ultrasound field upon turning the magnetic field On and Off; FIG. 3C as in FIG. 3B but in the presence of a regular natural RBC as a control. Scale bars, 20 μm.

FIG. 4A shows images illustrating the propulsion of the RBC motor in PBS, cell culture, serum, and whole blood. FIG. 4B The quantitative velocity of the RBC motor in different media at ultrasound voltage of 3 V and a frequency of 2.93 MHz. FIG. 4C Swimming behavior of the RBC motor in undiluted whole blood over 30 minutes. Scale bars, 10 μm. FIGS. 4D-4E Images showing the propulsion of the RBC motor in whole blood before FIG. 4D and after FIG. 4E a 24 hour incubation in the whole blood, respectively. Scale bars, 10 μm.

FIGS. 5A-5C show bright field microscopic images of J774 murine macrophage cells incubated for 30 minutes, with regular RBCs, RBC motors, and iron-oxide nanoparticles (Fe3O4 NPs, with equal amounts of iron to that of the RBC motors), respectively. FIG. 5D Quantitative analysis of macrophage uptake of RBC motors and iron oxide NPs determined by ICP-MS measurements.

FIGS. 6A-6B are optical images of regular RBCs before and after the ultrasonic treatment, respectively. Scale bars, 2 μm. FIG. 6C is an absorption spectra of regular RBCs under ultrasound field with an applied frequency of 2.93 MHz and at different transducer voltages (0-6 V). FIG. 6D is the relative hemolysis of regular RBCs under various ultrasound transducer voltages.

FIG. 8A shows optical image of the multicargo (MNPs-QDs-DOX)-loaded RBC micromotors. Fluorescence images of the cargo-loaded RBC micromotors in FIG. 8B QDs channel, FIG. 8C DOX channel, and FIG. 8D overlay of the two channels. Glycerol was added (2 mg $mL^{-1}$) to prevent movement of the micromotors during imaging. Scale bar, 20 μm.

FIGS. 9A-9C show magneto-switchable guidance of ultrasound-powered, multicargo-loaded RBC micromotors. Time-lapse images, illustrating the movement of FIG. 9A MNPs-located RBC motor, and FIG. 9B RBC-based motor loaded with MNPs, QDs, and DOX, under an ultrasound field (voltage of 4 V and frequency of 2.4 MHz) oriented with an external magnetic field provided by manually rotating a handheld magnet. FIG. 9C shows velocity of RBC motors without payloads (grey bars) and multicargo-loaded RBC motors (purple bars) using different ultrasound volt-ages at a frequency of 2.4 MHz. Scale bars, 20 μm. Error bars were estimated as three times the standard deviation (n=3 RBCs).

FIGS. 10A-10D show magnetically guided and ultrasound-powered transport of therapeutic and imaging agents in a multicargo-loaded RBC motor through a complex microchannel network. Actual time-lapse images illustrating the movement of multicargo-loaded RBC-based micromotors. FIG. 10A from the microchip inlet sample reservoir into the linear microfluidic channel, FIG. 10B in the Y-shaped microchip network, and FIG. 10C in the T-shaped microchip network (moving from positions 1 to 3). FIG. 10D Actual time-lapse image illustrating the magnetic control of the RBC motor in a linear microfluidic channel. Arrows indicate the direction of the movement. Scale bars, 20 μm.

DETAILED DESCRIPTION

Figure 2A:
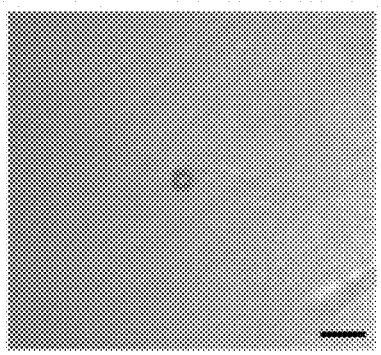
FIGS. 2A-2F shows the propulsion performance of RBC motors of an embodiment of the invention. The RBC motor, suspended in PBS solution, was subjected to various external stimulus conditions, including FIG. 2A without any stimulus.

The invention provides in an embodiment a cellular micromotor comprising a cell having a plurality of magnetic particles contained therein. In embodiments, the cell is a red blood cell. In embodiments, the plurality of magnetic particles are magnetic nanoparticles having a diameter from about 1 nm to 100 nm. In embodiments, the plurality of magnetic particles are iron oxide nanoparticles. In embodiments, the cellular micromotor further comprises a therapeutic agent or an imaging agent. In embodiments, the cellular micromotor further comprises a therapeutic agent and an imaging agent.

The invention provides in certain embodiments a method for producing a cellular micromotor, the method comprising encapsulating a plurality of magnetic particles within a cell, wherein the cell is a red blood cell, wherein the plurality of magnetic particles are magnetic nanoparticles having a diameter from about 1 nm to 100 nm, further comprising encapsulating a therapeutic agent and/or an imaging agent within the cell.

The invention provides in an embodiment a method for producing a cellular micromotor wherein the encapsulation step comprises providing the cell; permeabilizing the cell; and exposing the permeabilized cell to a plurality of magnetic particles, wherein the permeabilizing step comprises suspending the cell in a hypotonic solution, wherein the plurality of magnetic particles, the therapeutic agent, and the imaging agent are encapsulated contemporaneously with one another.

The invention provides in an embodiment a method for controlling movement of a cellular micromotor selectively exposes a cell having a plurality of magnetic particles contained therein to an external magnetic field; and propelling the cell in a controlled manner using acoustics, wherein the external magnetic field influences and guides movement of the cell, wherein the acoustics are ultrasound. FIG. 1A is a schematic illustration of magnetically-guided, ultrasound-propelled RBC micromotors in whole blood.

The invention provides in an embodiment a method for diagnostic imaging using a living cell micromotor selectively exposes a cell having a plurality of magnetic particles and an imaging agent contained therein to an external magnetic field; propelling the red blood cell in a controlled manner using acoustics, wherein the external magnetic field influences and guides movement of the cell; and imaging the imaging agent.

The invention provides in an embodiment a method of treatment using a living cell micromotor selectively exposes a cell having a plurality of magnetic particles and a therapeutic agent contained therein to an external magnetic field and an ultrasound acoustical field to propel; and the cell in a controlled manner to a site in need of therapeutic treatment.

As used herein, "cell" means any living cellular organism, or the intact cell membrane thereof, which can be permeabilized to receive and retain magnetic particles. An exemplary cell is a red blood cell (RBCs, also referred to as erythrocytes), white blood cells, macrophages, pluripotent stem cells (native, induced or engineered). In embodiments, the cell can have an average diameter of 0.1-100 µm, 1-50 µm, or 6-8 µm.

As used herein, "magnetic particle" means any particle that exhibits substantial magnetic properties (e.g. diamagnetic, paramagnetic, ferromagnetic, antiferromagnetic, ferrimagnetic, antiferrimagnetic, or superparamagnetic properties). In some embodiments, the magnetic particles comprise a metal selected from iron, cobalt, zinc, cadmium, nickel, gadolinium, chromium, copper, manganese, and their oxides. In some embodiments, the magnetic particles comprise any magnetic alloy such as permalloy, neodymium alloy, alnico, bismanol, cunife, fernico, heusler alloy, mkm steel, metglas, samarium-cobalt, sendust, or supermalloy. In some embodiments, the magnetic particles are a magnetic alloy and comprise a metal selected from gold, silver, platinum, and copper. In some embodiments, the magnetic particles comprise a free metal ion, a metal oxide, a chelate, or an insoluble metal compound. In some embodiments, the magnetic particles comprise $Fe_3O_4$, $Fe_2O_3$, $Fe_2O_4$, $Fe_xPt_y$, $Co_xPt_y$, $MnFe_xO_y$, $CoFe_xO_y$, $NiFe_xO_y$, $CuFe_xO_y$, $ZnFe_xO_y$, and $CdFe_xO_y$, wherein x and y vary between 1 and 6 depending on the method of synthesis. In some preferred embodiments, the magnetic particles are selected from the group consisting of monocrystalline iron oxide nanoparticle and superparamagnetic iron oxide nanoparticles. In embodiments, the magnetic nanoparticles have a diameter from about 1 nm to 100 nm. Magnetic particles are distinguished from nonmagnetic particles. Nonmagnetic particles may not necessarily be completely nonmagnetic in nature, but may include materials that are weakly magnetic, very weakly paramagnetic or diamagnetic in nature. For example, the water that is commonly detected and imaged in magnetic resonance systems is detected because of the nuclear magnetic resonance of the water. Because the magnetism of the water is extremely weak relative to the magnetic particles described herein, however, water and the other weakly magnetic materials may be regarded as nonmagnetic particles.

As used herein, "imaging agent" means any substance, element, molecule, functional group, compound, fragments thereof or moiety that facilitates detection, imaging, and/or monitoring of a cellular micromotor. Examples of suitable imaging agents include, for example, magnetic resonance imaging contrast agents (e.g. gadolinium chelating agents such as gadolinium-DTPA), computed tomography imaging agents (e.g. heavy metal such as iron chelates), optical imaging agents (e.g. near-infrared optical imaging agents such as Cy 5.5, indocyanine green and its derivatives, spectrally resolvable inorganic fluorescent semiconductors nanocrystals such as quantum dots (e.g. CdTe quantum dot), etc.), radioisotopes (e.g. $^3H$, $^{14}C$, $^{18}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$, etc.), and the like.

As used herein, "therapeutic agent" means any substance, element, molecule, functional group, compound, fragments thereof or moiety capable of treating a disease or ameliorating a symptom associated therewith. Appropriate therapeutic agents can be selected by a person of ordinary skill based upon the particular disease and the particular molecule, cell, or tissue being targeted. That is, the choice of a particular therapeutic agent depends on the particular target molecule, cell, or tissue and the biological effect that is desired to evoke. Non-limiting examples of therapeutic agents may include chemotherapeutic agents, immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. In some embodiments, the therapeutic agent is a chemotherapeutic agent useful in the treatment of cancer. The chemotherapeutic agent can be, for example, a cytotoxic agent that affects rapidly dividing cells in general, or it may be a targeted agent that affects the deregulated proteins of cancer cells. The chemotherapeutic agent can be, for example, an alkylating agent, an anti-metabolite, an anti-tumor antibiotic, an anti-cytoskeletal agent, a topoisomerase inhibitor, an anti-hormonal agent, a photodynamic therapeutic agent, or a combination thereof. In an exemplary embodiment, the chemotherapeutic agent is the anti-cancer drug doxorubicin.

Throughout the specification various references are cited which are incorporated in their entirety herein by reference. Many modifications of the embodiments of the present disclosure will come to mind to one skilled in the art to which the disclosure pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

Example 1

RBC motors were prepared using a hypotonic dilution/encapsulation method to load iron oxide nanoparticles (20 nm) into RBCs (FIG. 1B).[37] In the experiment, the RBCs were briefly incubated with citrate-stabilized iron-oxide nanoparticles in hypoosmotic lysing buffer to undergo a hypotonic hemolysis process at low temperature (4° C.). It has been reported that the influx of fluid creates pores with a diameter of up to 100 nm in the RBC membrane.[38] These nanopores allow for inward diffusion of the magnetic nanoparticles from the surrounding medium into the cell and in parallel allow for outward diffusion of intracellular hemoglobin protein. The cells were held at low temperature for one hour so that the inner and outer particle concentrations reach equilibrium. Upon equilibrium, the solution reached isotonicity, when the cell membrane resealed by restoration of osmolarity. The temperature was then increased to 37° C. and the encapsulated magnetic nanoparticles were trapped inside the RBCs. Such loading protocol resulted in efficient encapsulation of magnetic nanoparticles into cells while minimizing damage to the cell membrane. The optical microscope image in FIG. 1C demonstrates that the RBC motors mostly retain the characteristic erythrocyte shape with a diameter of 6-8 μm. The transmission electron microscopy (TEM) image in FIG. 1D shows the magnetic nanoparticles as black spots within the RBC, located primarily inside the cell. During the hypotonic process, the nanoparticles aggregate asymmetrically within the RBCs into large magnetic particles, 39-41 which reflects the interaction between the nanoparticles and the remaining hemoglobin proteins to form an agglomerate. Such asymmetric distribution of the magnetic nanoparticle aggregates provides a net magnetization to the cellular structure that subsequently allows magnetic alignment under an external magnetic field.

Figure 2B:
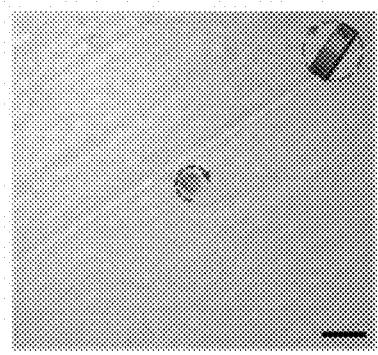
Figure 2C:
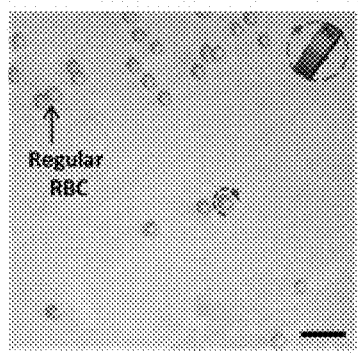
Figure 2D:
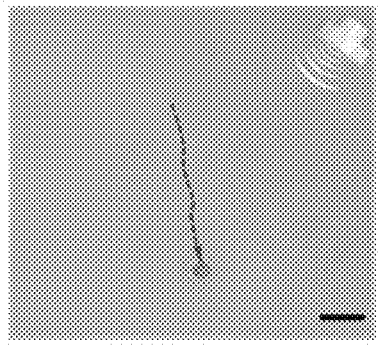

The RBC motors are acoustically powered and magnetically guided by an applied, external magnetic field. In order to prove that the RBC motors hold efficient guided motion under the combination of ultrasound and magnetic fields, a set of control experiments was conducted under different combinations of these external stimuli. FIG. 2A shows that the position of the RBC motor remained static in the absence of both ultrasound and magnetic fields. Application of a rotating magnetic field to the RBC motor, in the absence of ultrasound field, resulted in corresponding rotation of the motor, yet without its displacement (FIG. 2B), reflecting that the magnetic field affects only the orientation of the magnetic nanoparticles inside the RBC motor. Such magnetically-driven rotation was not observed for regular RBCs that do not contain internal magnetic nanoparticles (FIG. 2C). Application of an ultrasound field alone to the RBC motor led to directional motion of the motor, as displayed by the tracking line in FIG. 2D. It has been well documented that blood cells and microorganisms migrate toward pressure nodes under the ultrasound field.[33] However, such responses of regular cells are different from the controlled propulsion of MNPs-loaded RBC motors.

Figure 2E:
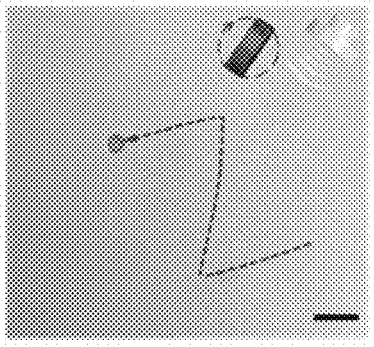
Figure 2F:
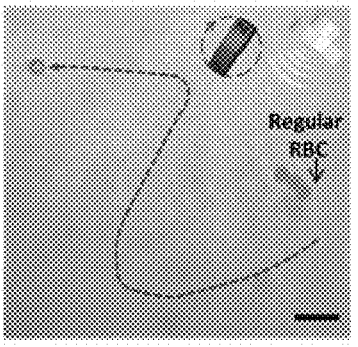

As illustrated in FIG. 2E, the simultaneous application of both the ultrasound and magnetic fields results in a guided motion of the RBC motor, reflecting the reversible alignment of the magnetization vector (discussed below). In order to confirm that this guided motion is selective to the RBC motors and not to other co-existing micro-objects, additional control experiments were performed by using regular RBCs (non-magnetic) as a negative control. FIG. 2F and corresponding Supplementary Video S1 illustrate that when both ultrasound and magnetic fields were applied to the system containing the regular and magnetic RBCs, only the RBC motors exhibited controlled motion (with a "Z" shape trajectory).

Figure 3A:
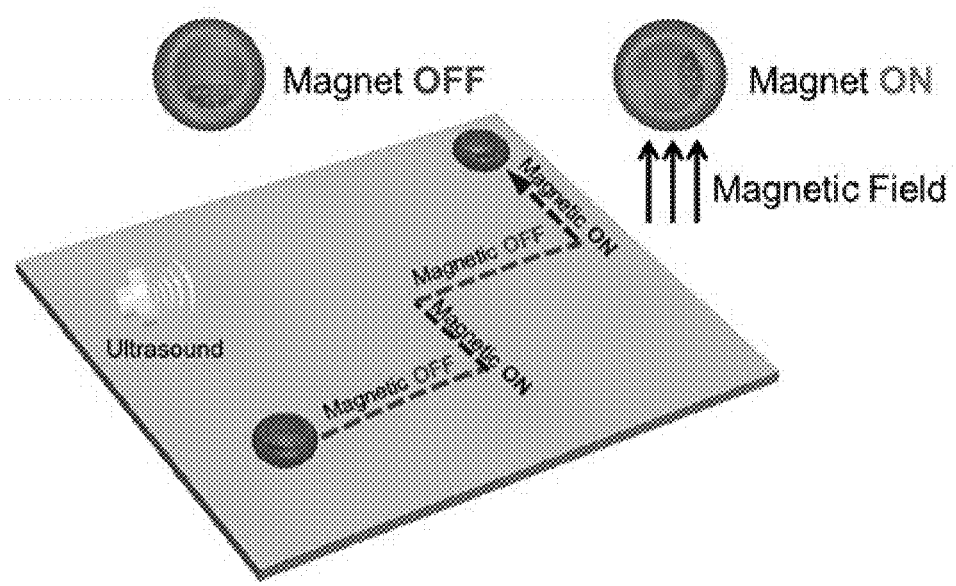
FIGS. 3A-3C show a magneto-switchable guidance of ultrasound-powered RBC motor of an embodiment of the invention.
Figure 3B:
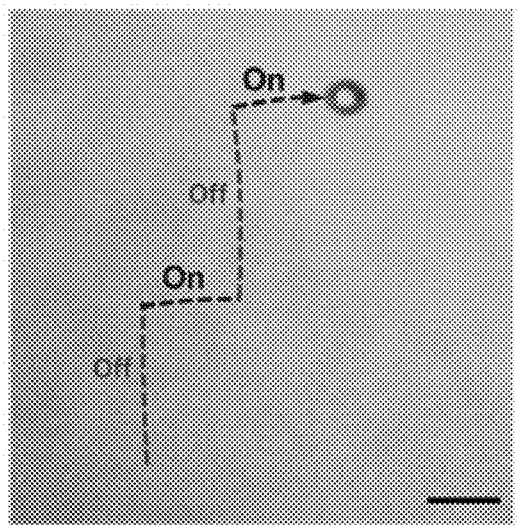
Figure 3C:
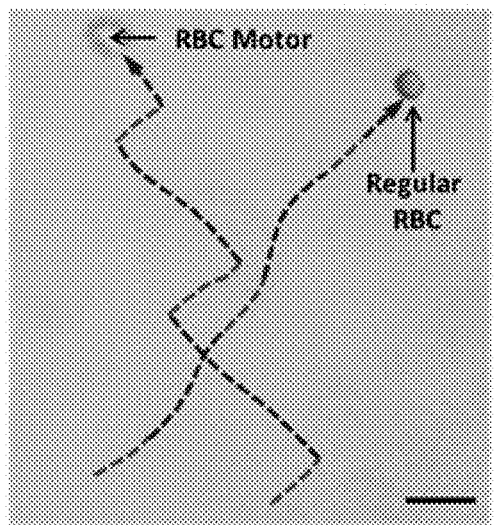

The magneto-switchable guidance of the RBC motor is demonstrated in FIG. 3. Application of the magnetic field (while the ultrasound power is on) provides a net magnetization that enables magnetic alignment and reversible guidance under the acoustic propulsion (FIG. 3A). The time-lapse image in FIGS. 3B-3C illustrates such reversible, magneto-switchable, controlled acoustic propulsion. The on/off magnetic switching allowed the motion of the RBC motor to be periodically re-oriented (FIGS. 3B-3C). Compared with the controlled movement of the RBC motor (FIG. 3B), the natural RBC exhibited no significant change in direction upon turning the magnetic field on or off (FIG. 3C). The switchable behavior of the RBC motor observed in FIGS. 3A-3C demonstrate the crucial role of the magnetic nanoparticles in controlling the direction of the ultrasound-powered RBC motor.

The ultrasound propulsion of the RBC motor is believed to be caused by an asymmetric distribution of the encapsulated magnetic nanoparticles inside the RBC motor (that leads to asymmetric intracellular density gradient) as well as the inherent asymmetric geometry of the RBC. Further, the asymmetry of the magnetic particles within the RBC creates a net magnetization within the cell in the presence of the magnetic field. The latter aligns the magnetization vector to become parallel with the field, altering the direction of the asymmetry. The magnetic orientation of the RBC motors can thus be switched 'On' and 'Off' by applying an external magnetic field. This data clearly indicates that encapsulating magnetic nanoparticles into the RBC motors, along with application of magnetic field, are useful for creating guided motion under the ultrasound field.

Figure 4A:
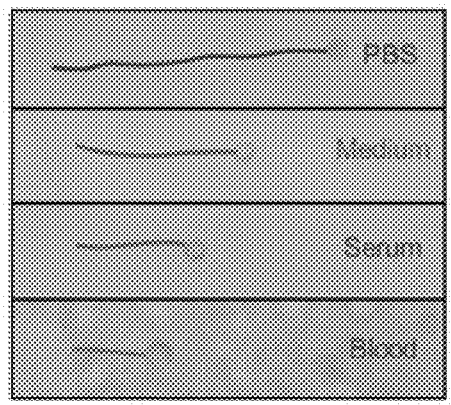
FIGS. 4A-4E show movement of RBC motors in various media of an embodiment of the invention.
Figure 4B:
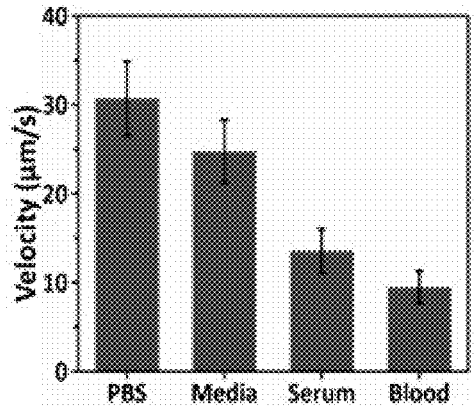

For practical biomedical applications, it is useful to test the propulsion performance of the RBC motor in relevant biological environments.[42] As illustrated in FIG. 4A, the RBC motors can operate readily in diverse media ranging from PBS buffer solution to undiluted whole blood. The ultrasound-powered RBC motors display a linear movement under the magnetic alignment. The 3 second track lines of such movement (FIG. 4A) indicate that the speed of the RBC motor decreased from 16 μm/s in the PBS solution to 13, 12, and 5 μm/s in the cell medium, serum, and whole blood, respectively, reflecting the increased environmental viscosity of these biofluids. The average speeds of the RBC motor in different biological media are measure and displayed in FIG. 4B. While these media affect the motor speed, the RBC motor still moves efficiently in the different environments, indicating the robustness of the motor for diverse biomedical applications.

Figure 4C:
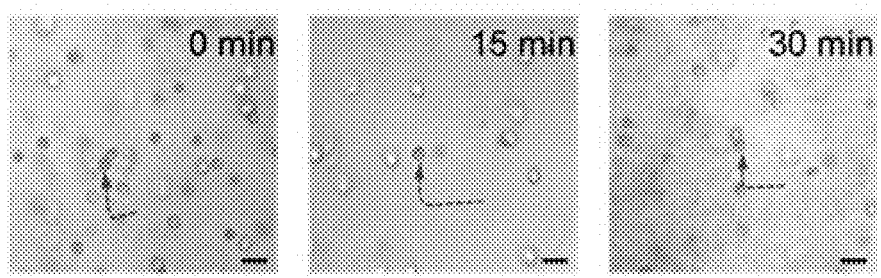
Figure 4D:
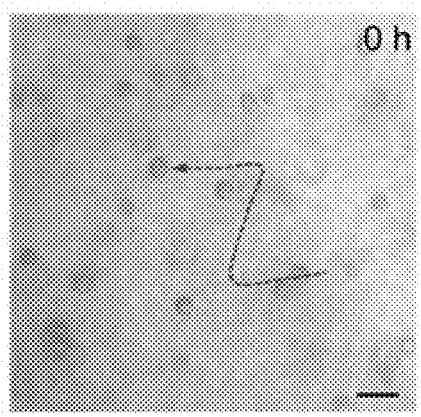
Figure 4E:
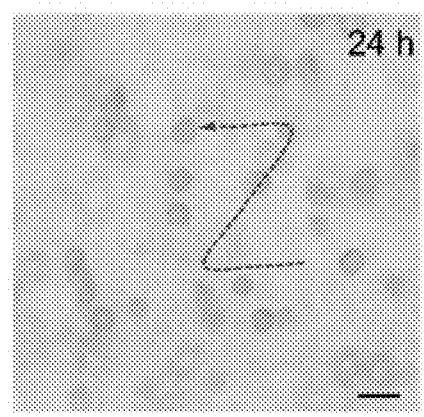

Of particular biomedical significance is the efficient propulsion and behavior of the RBC motor in undiluted whole blood. Most of the previous micromotor studies in biological fluids were focused on serum or highly diluted blood samples. Ghosh reported recently the magnetically actuated movement of cytocompatible ferrite-coated helical nanohelices in whole blood.[36] The RBC motor displayed magnetically-guided movement in undiluted whole blood over both short and long periods, consistent with the long life span of natural RBCs.[43] For example, the time-lapse images in FIG. 4C illustrates controlled movement of RBC motors through whole blood at 15 minute intervals over a 30 minute period. During this prolonged operation the motor displayed not only controllable movement with orthogonal turning, but also a negligible change of speed (14 μm/s at 0 minute, 13 μm/s at 15 minute, and 14 μm/s at 30 minute). FIG. 4D illustrates such propulsion of the RBC motor in whole blood along a predetermined Z-shaped trajectory. To demonstrate their resistance to biofouling, the RBC motor was incubated in undiluted whole blood for 24 hours followed by testing its performance. As shown in FIG. 4D-4E, the motor exhibits a similar magnetically-guided acoustic propulsion before and after the incubation; the "Z" trajectory of the RBC motor and the migration of regular RBCs with a speed of 5 μm/s can be observed. Note that such long immersion in whole blood has a minimal effect upon the speed of the RBC motor (12 vs 11 μm/s, before vs after the incubation), reflecting the absence of protein biofouling and salt-etching effects on the motor behavior. Overall, the data of FIG. 4 clearly indicates that RBC motor can operate in diverse environments, confirming the protection of the magnetic nanoparticles by the RBC membrane.

Figure 5A:
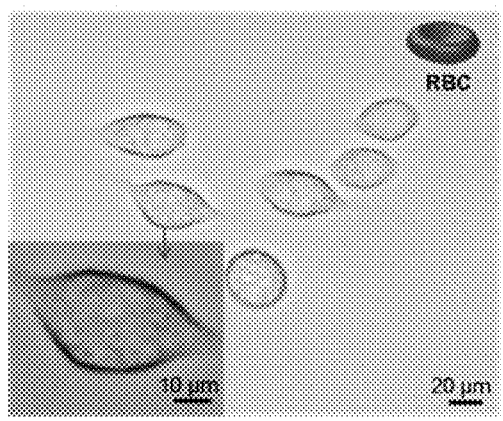
FIGS. 5A-5D show a macrophage uptake study to illustrate the biocompatibility of RBC motors of an embodiment of the invention.
Figure 5B:
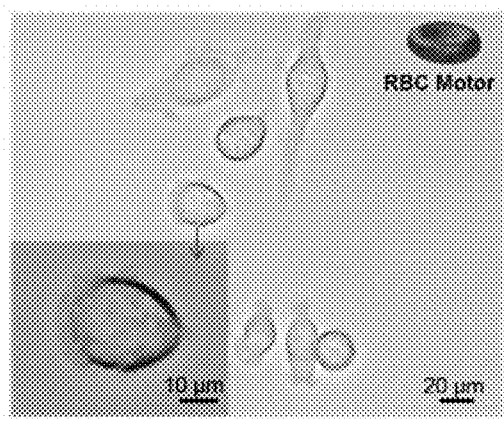
Figure 5C:
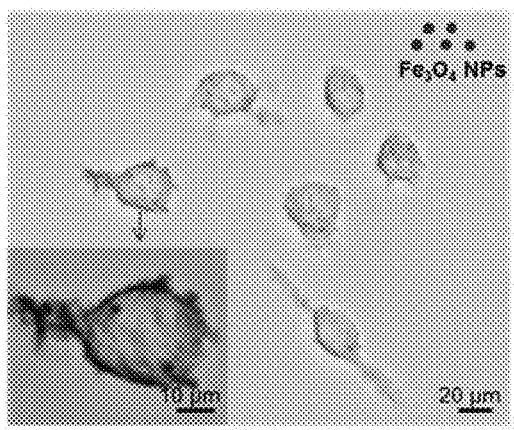
Figure 5D:
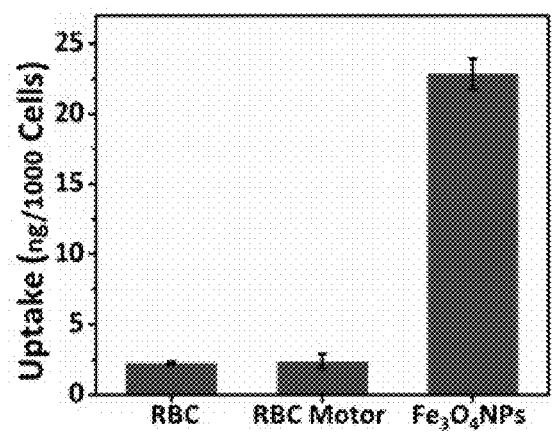

An important feature of the RBC motor is its anti-phagocytosis capability against macrophages which is crucial for evading the immune attack for prolong lifetime in the bloodstream. Given that the RBC motor retains intact membrane structure and antigens of natural RBCs including CD47 that prevents phagocytosis by macrophages through its interaction with inhibitory receptor SIRPα.[44,45] Therefore, the RBC motor is expected to share the functionality of natural RBCs. To investigate the biocompatibility of the RBC motor, a macrophage uptake study was carried out by cultivating the J774 murine macrophage cells with RBC motors or unencapsulated magnetic nanoparticles for 1 hour. To establish samples with equal amounts of iron, the magnetic nanoparticles were obtained from same amount of RBC motors which are completely lysed by the addition of Triton X-100. The macrophages with natural RBCs were cultivated as a background control, which showed negligible uptake of RBCs (FIG. 5A). Similar to natural RBCs, the RBC motors showed inhibited macrophage uptake as well (FIG. 5B). In contrast, the incubation of macrophages with unencapsulated magnetic nanoparticles resulted in a significant number of dark spots in the intracellular and perinuclear regions of the cells, indicating that the magnetic nanoparticles were actively taken up by the cells (FIG. 5C). Inductively-coupled plasma/mass spectrometry (ICP-MS) analysis was conducted to further quantify the iron uptake by the macrophage cells. As shown in FIG. 5D, an uptake of 22.88 ng iron per 1000 cells was observed from the magnetic nanoparticles, while the RBC motors had an uptake of 2.38 ng per 1000 macrophage cells. The near 10-fold reduction in the amount of iron clearly demonstrates that the RBC motor can effectively inhibit the uptake by the macrophage cells. The inhibition is largely due to the immunosuppressive antigens of the RBC membrane present on the RBC motors; the encapsulation of magnetic particles exhibits a negligible effect on the stealthy properties of the RBC.

Figure 6A:
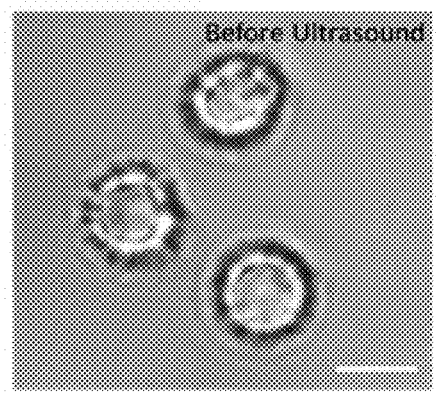
FIGS. 6A-6D show tolerability of regular RBCs under ultrasound operations of an embodiment of the invention.
Figure 6B:
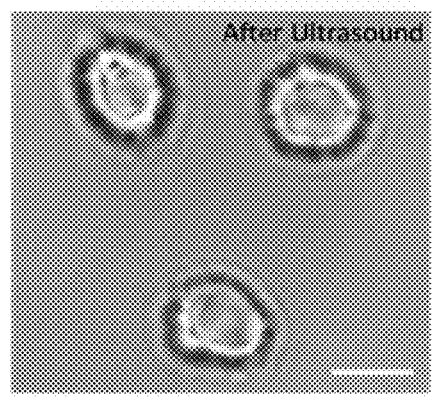
Figure 6C:
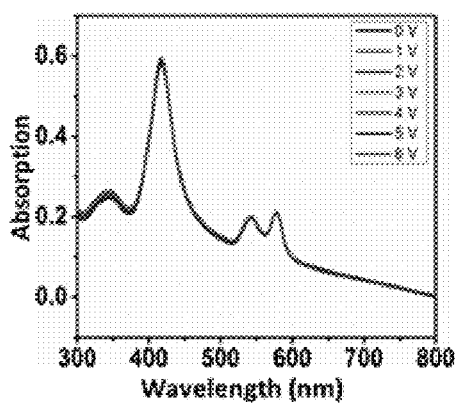
Figure 6D:
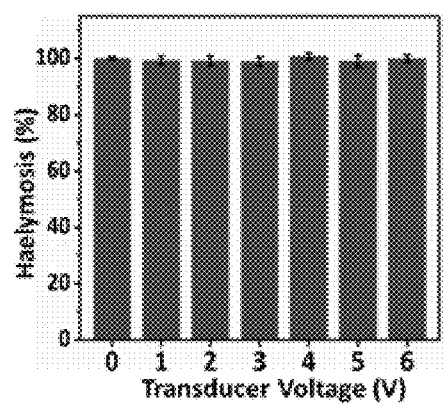

To test the tolerability of regular RBCs to the long period of ultrasound treatment, the properties of natural RBCs propelled by ultrasound at different transducer voltages (1-6 V) was examined for a period of 1 hour. The images of FIGS. 6A-6B show a 1% suspension of regular RBCs before and after the ultrasound treatment, respectively. The geometry of RBCs exhibited negligible change after the treatment, indicating that the ultrasound field did not cause adverse effect on the RBCs. Moreover, the absorption spectrum of regular RBCs, over the 300-800 nm wavelength range, showed no detectable change at various ultrasound powers (FIG. 6C). The ultrasound-treated regular RBCs were next subject to hemolytic lysis to quantify the remaining hemoglobin within these cells by measuring the hemoglobin absorbance at 540 nm. All hemoglobin was retained inside the cells after the ultrasound treatment, corresponding to near 100% hemolysis after the hemolytic treatment (FIG. 6D). Such negligible change in the degree of hemolysis further confirms the stability of regular RBCs under the ultrasound field.

The invention provides a cellular, such as an RBC-derived, approach for developing a new generation of cell-based micromotor that is powered by ultrasound and activated by a magnetic field. The RBC motor was fabricated by loading magnetic nanoparticles into natural RBCs. Switchable guided propulsion of RBC motors can be achieved by using a combination of the ultrasound and magnetic fields. The RBC motors can perform controlled propulsion in undiluted whole blood over extended periods with no apparent biofouling. The inhibited macrophage uptake confirms the biocompatibility of the RBC motors. The ability to load natural RBCs with a variety of functional components,[46] together with the efficient propulsion in a broad spectrum of biological fluids, provides multifunctional cell-based micromotors for a variety of in vitro and in vivo biomedical applications, and for bridging the gap between synthetic motors and the biological world.

Materials and Methods

Synthesis of Citrate-Stabilized Magnetic Nanoparticles.

Citrate-stabilized Fe3O4 nanoparticles were synthesized using the previously reported protocol.[47] Briefly, a mixture of 0.43 g of FeCl2 and 0.70 g of FeCl3 was mixed in 40 mL of water, which was degassed with nitrogen before mixing under the protection of nitrogen. Subsequently, 2 mL of NH4OH were added to the mixture solution under vigorous stirring and heated at 80° C. for additional 30 minutes. The supernatant was discarded while the nanoparticles were obtained in the reaction flask using a magnet, and then fresh degassed water was added. Citric acid solution (2 mL, 0.5 g/mL) was added, and the reaction mixture was maintained at 95° C. for 90 minutes. The reaction mixture was allowed to cool to room temperature under nitrogen. The nanoparticle suspension was washed three times with deionized water and then collected for the subsequent use.

Encapsulation of Magnetic Particles in RBCs.

Fresh RBCs were collected from six-week-old male ICR mice and anti-coagulated with ethylenediamine tetraacetate. The cells were rinsed three times with PBS (300 mOsm, pH 8). For encapsulating magnetic nanoparticles into the RBCs, 300 µL suspension of RBC and 300 µL suspension of citrate-stabilized iron-oxide nanoparticles were mixed, which led to a hypotonic condition (final osmotic pressure in RBC suspension, 100-160 mOsm). The RBCs were incubated under stirring at 4° C. for 1 h. The loaded RBCs were washed three times with PBS (300 mOsm, pH=8) at room temperature to remove the free hemoglobin and excess Fe3O4 nanoparticles. The resulting RBCs were resealed by incubation in 100 mL PBS at 37° C. for 1 h.

Ultrasound Equipment.

The ultrasound experiments were carried out in a cell, as was reported previously.[48,49] The cell was made in a covered glass slide (75×25×1 mm). A piezoelectric transducer (PZT), consisting of a 0.5 mm thick ring with a 10 mm outside diameter and 5 mm inner diameter was attached to the bottom center of the glass slide to create the ultrasonic field. The continuous ultrasound sine wave was applied through the PZT, via an Agilent 15 MHz arbitrary waveform generator, which was connected to a power amplifier. The continuous sine waveform had a frequency of 2.93 MHz and a voltage amplitude varied between 0 and 10.0 V, as needed for controlling the intensity of the ultrasonic wave. The electric signal was monitored using a 20 MHz Tektronix 434 storage oscilloscope.

Example 2

Figure 7:
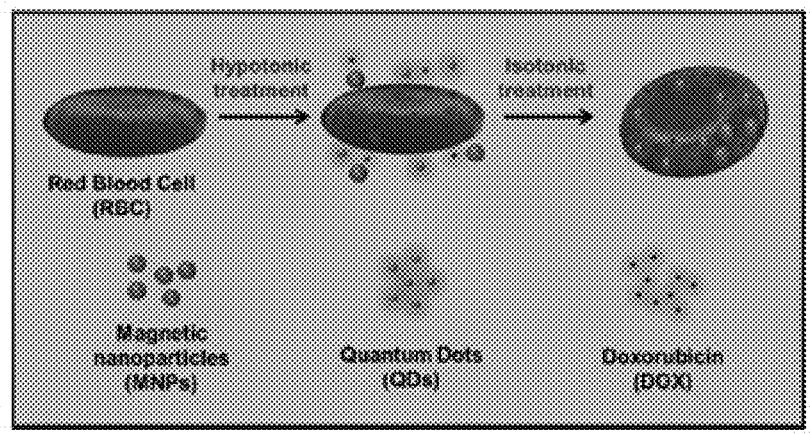
FIG. 7 shows schematic preparation of multicargo-loaded RBC micromotors towards theranostic applications. RBC cells are concurrently loaded with QDs imaging nanocrystals, the anti-cancer drug doxorubicin (DOX), and magnetic $Fe_3O_4$ nanoparticles through a hypotonic dilution based encapsulation method.

Multicargo-loaded, RBC-based micromotors are prepared by simultaneously loading water-soluble CdTe QD nanocrystals, the chemotherapy drug DOX, and iron oxide magnetic nanoparticles (MNPs) into RBCs using a hypotonic dilution based encapsulation method (FIG. 7). The resulting micromotors are able to convert acoustic energy into motion due to the uneven distribution of the MNPs within the RBC. The resulting multicargo-loaded RBC micromotors are thus propelled by the pressure gradient generated by an applied ultrasonic field due to the asymmetric distribution of MNPs within the RBCs, which enables magnetic guidance under the acoustic propulsion. The multicargo-loaded RBC micromotor presented here offers a new mobile platform for potential theranostic applications, capable of imaging a disease, delivering a drug, and monitoring the therapeutic response. Providing theranostic systems with efficient guided and controlled motion towards predetermined disease locations can potentially enhance the power of such platforms towards improving applicability and efficacy. Yet, such development requires understanding of the influence of the encapsulating therapeutic and imaging cargos upon the propulsion behavior and transport properties of the RBC motor. The following sections will thus report on the characterization of the RBC motors, loaded with diagnostic imaging agents and therapeutic drugs, and will demonstrate that such cargo loading does not compromise the locomotion or biocompatibility of these biomimetic motors.

The multicargo-loaded, RBC-based micromotors were prepared by simultaneously encapsulating three components through a hypotonic dilution method.[76,77] These include iron-oxide magnetic nanoparticles (MNPs, 20 nm diameter) that enable the controlled movement of the RBC micromotors, hydrophilic CdTe QDs that provide imaging via fluorescence emission ($\lambda_{em}$=510 nm) with high stability against photobleaching, and the chemotherapy drug DOX that serves as a model therapeutic payload and as an additional imaging agent (by its inherent self-fluorescence at $\lambda_{em}$=580 nm). The concurrent encapsulation of these three components thus permits controlled navigation, imaging, and drug delivery, which enables the multicargo-loaded RBC micromotors to serve as a potential mobile theranostic tool. Cargo loading within RBCs has been reported previously,[76] but not in connection to micromotor movement and transport.

To load the functional components into RBCs, the cells were first subjected to hypotonic dilution followed by an isotonic treatment, as illustrated in FIG. 7. Briefly, RBCs were mixed with an aqueous solution containing MNPs, hydrophilic QDs, and DOX by hypotonic conditioning (final osmotic pressure in RBC micromotor suspension, 140-160 mOsm) at 4° C. for one hour. This hypotonic treatment of RBCs leads to the formation of about 100 nm diameter pores in the membrane,[73] resulting in the exchange of intracellular hemoglobin for the extracellular components (drug and imaging agents). The low temperature prolongs the lifetime of these pores and allows the osmolarity between the inner cell and the surrounding medium. Subsequently, the RBC membrane is returned to isotonicity by incubation in PBS at 37° C. for one hour, encapsulating the multiple entities within the cells. This hypotonic loading strategy allows efficient encapsulation of the target components in one simple step, with negligible adverse effects on the cells. The internalization of the MNPs into RBC, demonstrated by TEM imaging, indicated the encapsulation of a high amount of MNPs and—more importantly—their aggregation within the cells (which was previously demonstrated[69]). The aggregated MNPs within the RBC provide the required density necessary to achieve an acoustic response after applying the US field.[78]

Figure 8A:
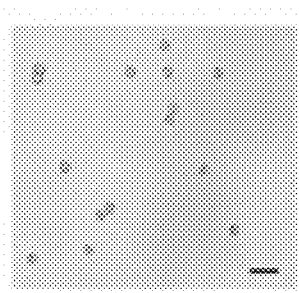
FIGS. 8A-8D show co-localization of multiple cargos within RBCs.
Figure 8B:
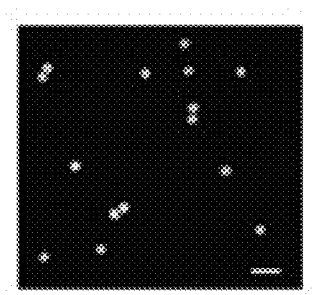
Figure 8C:
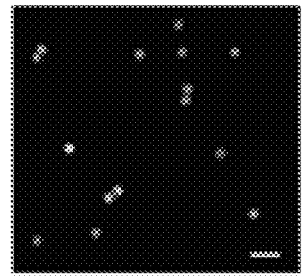
Figure 8D:
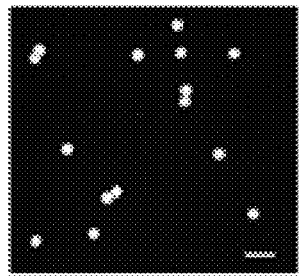

Optical and fluorescent images were carried out to examine the structural integrity of the multicargo-loaded RBC micro¬motors and the simultaneous encapsulation of the therapeutic and imaging agents. FIG. 8A shows the optical image of the multicargo-loaded RBC micromotors after the encapsulation process. This image (along with the additional data given below) demonstrates that the RBC micromotors retain their characteristic structure and shape with diameters of ~6-8 μm and have no apparent damage due to the cargo encapsulation processes. The fluorescence images, shown in FIGS. 8B-8D, confirm the successful incorporation of QDs and DOX into the RBC micromotor (via the strong fluorescence of both agents). While FIG. 8B shows the emission of green fluorescence ($\lambda_{em}$=510 nm) due to the presence of the CdTe QDs inside the cells, FIG. 8C displays the emission of red fluorescence from the DOX ($\lambda_{em}$=580 nm) within the RBCs. Lastly, FIG. 8D shows the overlapped fluorescent images of QDs and DOX, which exhibit a significant degree of overlap, indicating effective co-localization of QDs and DOX within the same cells (glycerol was added to the suspension to prevent cell drifting during the imaging process for improved co-localization quality).

NPs within the RBC micromotors was determined. Such quantitative assay of DOX and QD uptake in the cells was conducted by lysing the membrane of the multicargo-loaded RBC micromotors. The RBC micromotors were solubilized in a Triton lysis buffer solution and incubated for 30 min in an ultrasound bath. Then, the optical and fluorescence images of the multicargo-loaded RBC micromotors before and after lysis treatment were compared. After the lysis treatment, the fluorescence intensity of the released DOX and QDs was interpolated into the corresponding fluorescence intensity calibration plots, from which the loading yield of DOX and QDs was calculated. Taking into account that there were about 115 RBC motors per 0.5 μL of the cell suspension, the estimated drug loading yield was 5.3×10$^7$ DOX molecules per RBC micromotor (corresponding to 0.05 pg DOX/RBC), which is within the previously reported range[76] and is sufficient for potential therapeutic use.[74] Similarly, the amount of QDs per RBC micromotor was found to be 9.6 pg. Inductively coupled plasma/mass spectrometry (ICP-MS) analysis was also used for quantifying the encapsulated MNPs; this analysis resulted in 40 pg Fe per RBC micromotor.

Next, the ability of the RBC motors to transport multiple payloads in a rapid and controlled manner was demonstrated and that such multicargo loading did not compromise the locomotion of these biomimetic motors. The magnetically guided, ultrasound-powered movement of multicargo-loaded RBC micromotors was achieved by applying ultrasound and orienting them with a magnetic field. The ultrasound movement is driven primarily by the uneven distribution of the encapsulated MNPs within the RBC micromotor under the applied magnetic field.[79] Such asymmetric particle distribution inside the RBC motor results in an acoustic pressure gradient in the fluid causing the movement. Under a constant frequency (2.4 MHz) the RBC motors move to a levitation plane by the primary radiation force, and move within this plane due to the scattering acoustic waves. The contribution of different acoustic and fluid forces involved in this phenomenon has been described in a recent review.[80] Different groups have previously demonstrated that rigid metallic nanowires and biological materials move to the same levitation plane node.[78,81] The effect of the QD and DOX encapsulation on the propulsion of the RBC micromotors was investigated by comparing the motion of a MNPs-QDs-DOX-loaded RBC micromotor with that of a MNPs-loaded RBC micromotor. The time-lapse images in FIGS. 9A and 9B show that both RBC motors exhibited controlled motion, following similar predetermined trajectories under the magnetically guided ultrasound propulsion. The speed of these multicargo-loaded RBC micromotors remained nearly unchanged while orienting the magnetic field in the direction highlighted by blue dotted tracking line (15±2 μm s$^{-1}$ for MNPs-loaded RBC motor and 14±2 μm s$^{-1}$ for MNPs-QDs-DOX-loaded RBC motor) and in the direction indicated by the red dotted tracking line (14±1 μm s$^{-1}$ for MNPs-loaded RBC motor and 14±1 μm s$^{-1}$ for MNPs-QDs-DOX-loaded RBC motor). Such behavior reflects the minimal deleterious effect of the external magnetic field upon the propulsion force, and hence on the speed of the multicargo-loaded RBC motor. To further examine the effect of the QDs and DOX encapsulation on the ultrasound-driven movement of the motors, the speeds of MNPs-loaded RBC motors and MNPs-QDs-DOX-loaded RBC motors were investigated and compared under different ultrasound transducer voltages. As illustrated in FIG. 9C, the average speed of both motors increased upon increasing the ultrasound transducer voltage between 2 V and 8 V. For example, the speeds of MNPs-loaded RBC motors and MNPs-QDs-DOX-loaded RBC motors under different ultrasound voltages are quite similar (14 μm s$^{-1}$ vs. 15 μm s$^{-1}$ at 2 V, 31 μm s$^{-1}$ vs. 34 μm s$^{-1}$ at 4 V, and 60 μm s$^{-1}$ vs. 55 μm s$^{-1}$ at 8 V). These results confirm that the encapsulation of QDs and DOX into the RBC micromotors has a negligible effect upon their propulsion performance, and that these micromotors can deliver the drug and imaging agents at a rapid rate.

The ability to control of the directionality of the multicargo-loaded RBC micromotors is essential towards potential theranostic applications of the motors. Furthermore, the similarity of the channels with blood vessels makes these devices an excellent biomimetic platform for testing the performance of theranostic RBC motors. Herein, the high spatial directionality of the cargo-loaded RBC micromotor was demonstrated by their ability to transport the encapsulated QD imaging agents and DOX drug to a predetermined destination through a predefined route within a complex microchannel network. Three different polydimethylsiloxane (PDMS)-based microchip devices, with linear, Y-shaped, and T-shaped channels, were used to test the controlled movement of the multicargo-loaded, ultrasound-powered, magnetically guided RBC micromotors towards different predetermined sites in the microchip network. The time-lapse image in FIG. 10A, show such guided movement of an RBC micromotor from the inlet sample reservoir into the linear channel.

Similarly, the time-lapse images in FIGS. 10B-10C illustrate the guided propulsion of an RBC micromotor under ultrasound field in different sections of the Y-shaped and T-shaped microfluidic channels, respectively. The multicargo-loaded RBC motor displays efficient movement and motion control while entering these cross-sections, meeting the demands of rapid and precise transport of both cargo modalities to predetermined destinations. FIG. 10D illustrates the magnetic control of the direction of the multicargo-loaded RBC micromotor in the linear microfluidic chip by changing the orientation of a neodymium magnet. The motor could be magnetically guided to cross the channel and rapidly perform a sharp U-turn (upon changing the direction of the magnet), demonstrating the ability to change the direction of these multicargo-loaded micromotors to a specific site within the microchip. Overall, FIGS. 10A-10D clearly demonstrate that the micromotor displays efficient movement and effective spatial motion control within the narrow channels and the different reservoirs in the microchip, reflecting the precise magnetic guidance.

Furthermore, to evaluate the potential of multicargo RBC micromotors for theranostic application, we tested the ability of the motors to shield the toxicity of the loaded cargos. Specifically, the cellular viability of Human Umbilical Vein Endothelial Cells (HUVECs) was compared after incubating with free DOX (11.5 ng mL$^{-1}$), free QDs (0.2 ng μL$^{-1}$), free DOX+QDs, and multicargo RBC micromotors (loaded with the same concentrations of free DOX and QDs) using a colorimetric MTS assay. As shown in ESI FIGS. 9A-9C, free QDs showed negligible cytotoxicity, as expected due to the low concentration used. However, when the cells were incubated with free DOX or free DOX+QDs, the cell viability decreased to 19.7±6.6% and 19.0±8.3%, respectively, which could be explained by the high toxicity of the drug used in the study. In contrast, multicargo-loaded RBC micromotors exhibited three times lower toxicity compared to free DOX and free (DOX+QDs) over a 24 h incubation period. The observed toxicity of the multicargo-loaded RBC micromotors is likely due to the release of DOX from the motors during the incubation time. These promising results indicate that when chemotherapeutic drug is encapsulated inside the RBC motors, its toxic effect on healthy cells is significantly shielded by the RBC membranes, which make the RBC motors an attractive vehicle to deliver highly toxic therapeutic agents.

This example demonstrates the ability to load both therapeutic and imaging agents into an RBC-based micromotor and examined the influence of such multi-cargo loading upon the propulsion behavior, transport properties, and toxicity of these biomimetic motors. The cell-based, cargo-loaded micromotor was driven by ultrasound forces and guided by an external magnetic field. Such simultaneous encapsulation of an imaging agent and an anti-cancer drug within the same erythrocyte micromotor had a minimal effect upon its efficient propulsion behavior and biocompatibility. Precise transport of these therapeutic and imaging agents within the narrow microchip channel network was illustrated, indicating considerable promise for imparting directionality and mobility onto future theranostic systems. Such ability of the RBC micromotors to carry multiple functional cargos while retaining their powerful propulsion property makes these biomimetic micromotors an attractive multicargo delivery platform. The guided movement of biomimetic motors may lead to improved drug delivery efficiency and disease monitoring. Since a myriad of therapeutic and diagnostic agents can be encapsulated in the RBC motors, this work opens the door to a wide range of biomedical applications of multifunctional biomimetic micromotors, combining different modalities that simultaneously treat and monitor diseases.

Reagents and Solutions

Hydrophilic CdTe core-type COOH-functionalized quantum dots (QDs), iron(II) chloride tetrahydrate (FeCl$_2$-4H$_2$O), iron(III) chloride tetrahydrate (FeCl$_3$-4H$_2$O), citric acid monohydrate, doxorubicin hydrochloride (DOX), and propidium iodide (PI) were obtained from Sigma-Aldrich Chemical Inc. (St Louis, Mo.).

Equipment

An optical microscope (Nikon Eclipse Instrument Inc. 80i), coupled with a 20× objective, along with a Photometrics Cool-SNAP HQ2 CCD camera and Molecular Devices MetaMorph image analysis software, were used for capturing the optical images and the corresponding videos. The speed of the micromotors was measured using a MetaMorph tracking module and the results were statistically analyzed by using Origin software. The fluorescent measurements were completed in a Nikon Eclipse TE2000-S inverted optical microscope and captured with a Photometrics QuantEM:512SC EMCCD camera using MetaMorph image analysis software. Inductively coupled plasma-mass spectrometry (ICP-MS), (Thermoquest Finnigan Element 2 ICP—high-resolution mass spectrometer) was used for determining the iron content of the encapsulated MNPs in the RBC micromotors.

Preparation of the PDMS Microchannel

The microfluidic polydimethylsiloxane (PDMS) chips were fabricated using conventional soft lithography techniques. The chips consisted of a PDMS film (10 mm×30 mm) with 0.7 mm diameter reservoirs and a channel width of 50 μm for linear and T-shaped channels and 100 μm in the Y-shaped devices, with different channel lengths depending on the specific design. Soft lithography of PDMS was used to fabricate the microchannel structures. The mask was produced on transparent Mylar sheets using a high resolution (20 000-50 000 dpi) printing system (Fineline Imaging, Colorado Springs, Colo.). The master for soft lithography consisted of SU-8 (negative photoresist) patterned on a 4" silicon wafer. The surface was silanized with trichloromethylsilane (TCMS) vapor for about 30 min Then, Sylgard 184 PDMS (Dow Corning Corporation, Midland, Mich.) was prepared in a 10:1 ratio and poured over the master, degassed, and cured at 70° C. for 60 min. The microchip consisted of a PDMS channel and a glass wafer that were assembled after being exposed to an ultraviolet/ozone surface treatment in a PSD Pro Series benchtop UV cleaner (Novascan, Ames, Iowa) for 5 min. The microchannels were filled before use with 0.3 M NaOH for 5 min. The PDMS microchannels were then flushed with DI water at least 3 times to ensure the removal of any residual NaOH.

Synthesis of Iron Oxide Nanoparticles

Citrate-stabilized $Fe_3O_4$ nanoparticles were synthesized using a previously reported protocol.[75] Briefly, 0.70 g of $FeCl_3$ and 0.43 g of $FeCl_2$ were mixed in 40 mL of water. Then, 2 mL of $NH_4OH$ was added to the mixture under vigorous stirring and heated at 80° C. for 30 min. The supernatant was discarded while the nanoparticles were retained in the reaction flask using a magnet, and then fresh degassed water was added. Citric acid solution (2 mL, 0.5 g $mL^{-1}$) was added, and the reaction mixture was maintained at 95° C. for 90 min. The reaction mixture was allowed to cool to room temperature under nitrogen. The nanoparticle suspension was washed three times with deionized water.

Preparation of the Mnps-Qds-Dox-Rbc Micromotor

Fresh RBCs were obtained from six-week-old male ICR mice. The RBCs were diluted to 5% and washed three times by using PBS (300 mOsm, pH 7.2). After that, 1 mL of RBC was incubated with a mixture containing 0.3 mL of CdTe QDs solution (0.2 mg $mL^{-1}$), 0.45 mL of MNPs, and 0.15 mL of DOX solution (1 mg $mL^{-1}$). The incubation procedure in the hypotonic condition (final osmotic pressure in RBC micromotor suspension, 140-160 mOsm) was maintained at 4° C. for 1-2 h. Then, the loaded RBC motors were rinsed three times with PBS (300 mOsm, pH 7.2) to remove excess components and free hemoglobin. The membranes of the resulting RBC micromotors were restored by incubation in PBS (300 mOsm, pH 7.2) at 37° C. for 1 h. The solution of RBC motors was then stored in 4° C. for subsequent use.

Ultrasound Propulsion

The ultrasound-powered movement of the multicargo-loaded RBC micromotors was carried out using a previously described acoustic cell and covered with a glass slide, as reported previously.[82,83] The ultrasound field was provided by a piezoelectric transducer with a 10 mm outside diameter, 5 mm inner diameter and a thickness of 0.5 mm through an Agilent 15 MHz arbitrary waveform generator connected to a power amplifier. The piezoelectric transducer was attached to the bottom center of the microfluidic chip and a continuous sine waveform, with a frequency of 2.4 MHz and varied voltage amplitudes between 0 and 10.0 V, was applied to the transducer.

The application of a constant frequency (2.4 MHz) in this setup permits the RBC motors to move to a levitation plane. In this levitation plane, the RBC motors are moved due to the scattering acoustic waves produced at that constant frequency. Due to the uneven distribution of the MNPs within the RBC, the micromotors are able to convert acoustic energy into motion using a constant frequency.

Magnetic Guidance

The motors have been oriented in the direction of an external magnetic field produced by a neodymium magnet (NdFeB: 0.5 Tesla; 1"×1'×1").

Lysis of the Multicargo-Loaded, Rbc-Based Micromotors

Multicargo-loaded, RBC-based micromotors were solubilized in a Triton lysis buffer solution consisting of 1% Triton X-100 in 10 mM Tris-HCl (pH 7.4) supplemented with 100 mM NaCl and 2 mM EDTA, and incubated for 30 min in an ultrasound bath.

Microchip Experiment

Multicargo-loaded, RBC-based micromotors in the microchannels were operated by filling the microchip reservoirs and microchannels with a PBS buffer solution (300 mOsm, pH 7.2) containing the RBC motors.

Cellular Viability Assay

The cytotoxicities of free DOX, free QDs, free (DOX+QDs), and multicargo RBC-based micromotors against Human Umbilical Vein Endothelial Cells (HUVECs) were determined by MTS assay (CellTiter 96® $AQ_{ueous}$ One Solution Cell Proliferation Assay). Cells were harvested at 80% confluency and plated in 96-well plates at 1000 cells per well in 200 µL of media per well. Free DOX (11.5 ng $mL^{-1}$), free QDs (0.2 ng $µL^{-1}$), free (DOX+QDs), and RBC micromotors containing the same concentration of DOX and QDs were incubated with the cells for 24 h. Cells without drug were included in each experiment as controls. After 24 h incubation, 20 µL of CellTiter 96® $AQ_{ueous}$ were added to [3-(4,5-dimethylthiazol-2-yl)-5-(3-carboxymethoxy-phenyl)-2-(4-sulfophenyl)-2H-tetrazolium inner salt; MTS] solution reagent. The conversion of MTS into formazan by metabolically active cells indicated the extent of cell viability. After 1 h incubation at 37° C. in a humidified, 5% $CO_2$ atmosphere, the absorbance was measured at 490 nm using a microplate reader (Biotek Synergy MX, Mandel Scientific Inc.) for the quantification of cell viability. All of the assays were run in triplicate.

REFERENCES

1. Dreyfus, R.; Baudry, J.; Roper, M. L.; Fermigier, M.; Stone, H. A.; Bibette, J. Microscopic Artificial Swimmers. Nature 2005, 437, 862-865.
2. Paxton, W. F.; Kistler, K. C.; Olmeda, C. C.; Sen, A.; St. Angelo, S. K.; Cao, Y.; Mallouk, T. E.; Lammert, P. E.; Crespi, V. H. Catalytic Nanomotors: Autonomous Movement of Striped Nanorods. J. Am. Chem. Soc. 2004, 126, 13424-13431.
3. Wilson, D. A.; Nolte, R. J. M.; van Hest, J. C. M. Autonomous Movement of Platinum-Loaded Stomatocytes. Nat. Chem. 2012, 4, 268-274.
4. Weiss, P. S. Nanotechnology: A Molecular Four-Wheel Drive. Nature 2011, 479, 187-188.
5. Wang, J. Nanomachines: Fundamentals and Applications; Wiley-VCH: Weinheim, Germany, 2013.
6. Mei, Y. F.; Solovev, A. A.; Sanchez, S.; Schmidt, O. G. Rolled-up Nanotech on Polymers: From Basic Perception to Self-Propelled Catalytic Microengines. Chem. Soc. Rev. 2011, 40, 2109-2119.
7. Loget, G.; Kuhn, A. Electric Field-induced Chemical Locomotion of Conducting Objects. Nat. Commun. 2011, 2, 535.
8. van Rhee, P. G.; Rikken, R. S. M.; Abdelmohsen, L. K. E. A.; Maan, J. C.; Nolte, R. J. M.; van Hest, J. C. M.; Christianen, P. C. M.; Wilson, D. A. Polymersome Magneto-Valves for Reversible Capture and Release of Nanoparticles. Nat. Commun. 2014, 5.

9. Li, J.; Gao, W.; Dong, R.; Pei, A.; Sattayasamitsathit, S.; Wang, J. Nanomotor Lithography. Nat. Commun. 2014, 5.
10. Wu, J.; Balasubramanian, S.; Kagan, D.; Manesh, K. M.; Campuzano, S.; Wang, J. Motion-Based DNA Detection Using Catalytic Nanomotors. Nat. Commun. 2010, 1, 36.
11. Sengupta, S.; Patra, D.; Ortiz-Rivera, I.; Agrawal, A.; Shklyaev, S.; Dey, K. K.; Cordova-Figueroa, U.; Mallouk, T. E.; Sen, A. Self-Powered Enzyme Micropumps. Nat. Chem. 2014, 6, 415-422.
12. Ikezoe, Y.; Washino, G.; Uemura, T.; Kitagawa, S.; Matsui, H. Autonomous Motors of a Metal-Organic Framework Powered by Reorganization of Self-Assembled Peptides at Interfaces. Nat. Mater. 2012, 11, 1081-1085.
13. Solovev, A. A.; Sanchez, S.; Pumera, M.; Mei, Y. F.; Schmidt, O. G. Magnetic Control of Tubular Catalytic Microbots for the Transport, Assembly, and Delivery of Micro-objects. Adv. Funct. Mater. 2010, 20, 2430-2435.
14. Guix, M.; Mayorga-Martinez, C. C.; Merkoçi, A. Nano/Micromotors in (Bio)Chemical Science Applications. Chem. Rev. 2014, 114, 6285-6322.
15. Ismagilov, R. F.; Schwartz, A.; Bowden, N.; Whitesides, G. M. Autonomous Movement and Self-Assembly. Angew. Chem., Int. Ed. 2002, 114, 652-654.
16. Wang, W.; Duan, W.; Ahmed, S.; Mallouk, T. E.; Sen, A. Small Power: Autonomous Nano- and Micromotors Propelled by Self-Generated Gradients. Nano Today 2013, 8, 531-554.
17. Tottori, S.; Zhang, L.; Peyer, K. E.; Nelson, B. J. Assembly, Disassembly, and Anomalous Propulsion of Microscopic Helices. Nano Lett. 2013, 13, 4263-4268.
18. Wang, W.; Castro, L. A.; Hoyos, M.; Mallouk, T. E., Autonomous Motion of Metallic Microrods Propelled by Ultrasound. ACS Nano 2012, 6, 6122-6132.
19. Fischer P, Ghosh A. Magnetically actuated propulsion at low Reynolds numbers: towards nanoscale control. Nanoscale 3, 557-563 (2011). Fischer, P.; Ghosh, A. Magnetically Actuated Propulsion at Low Reynolds Numbers: Towards Nanoscale Control. Nanoscale 2011, 3, 557-563.
20. Schamel, D.; Mark, A. G.; Gibbs, J. G.; Miksch, C.; Morozov, K. I.; Leshansky, A. M.; Fischer, P. Nanopropellers and Their Actuation in Complex Viscoelastic Media. ACS Nano 2014, 8, 8794-8801.
21. Zhang, L.; Hong, L.; Yu, Y.; Bae, S. C.; Granick, S. Nanoparticle-Assisted Surface Immobilization of Phospholipid Liposomes. J. Am. Chem. Soc. 2006, 128, 9026-9027.
22. Zhang, L.; Spurlin, T. A.; Gewirth, A. A.; Granick, S. Electrostatic Stitching in Gel-Phase Supported Phospholipid Bilayers. J. Phys. Chem. B 2005, 110, 33-35.
23. Love, K. T.; Mahon, K. P.; Levins, C. G.; Whitehead, K. A.; Querbes, W.; Dorkin, J. R.; Qin, J.; Cantley, W.; Qin, L. L.; Racie, T.; Frank-Kamenetsky, M.; Yip, K. N.; Alvarez, R.; Sah, D. W. Y.; de Fougerolles, A.; Fitzgerald, K.; Koteliansky, V.; Akinc, A.; Langer, R.; Anderson, D. G. Lipid-Like Materials for Low-Dose, in Vivo Gene Silencing. Proc. Natl. Acad. Sci. U.S.A. 2010, 107, 1864-1869.
24. Celiz, A. D.; Smith, J. G. W.; Langer, R.; Anderson, D. G.; Winkler, D. A.; Barrett, D. A.; Davies, M. C.; Young, L. E.; Denning, C.; Alexander, M. R. Materials for Stem Cell Factories of the Future. Nat. Mater. 2014, 13, 570-579.
25. Yang, F.; Cho, S. W.; Son, S. M.; Bogatyrev, S. R.; Singh, D.; Green, J. J.; Mei, Y.; Park, S.; Bhang, S. H.; Kim, B. S.; Langer, R.; Anderson, D. G. Genetic Engineering of Human Stem Cells for Enhanced Angiogenesis Using Biodegradable Polymeric Nanoparticles. Proc. Natl. Acad. Sci. U.S.A. 2010, 107, 3317-3322.
26. Hu, C. M.; Fang, R. H.; Luk, B. T.; Zhang, L. Nanoparticle-Detained Toxins for Safe and Effective Vaccination. Nat. Nanotech. 2013, 8, 933-938.
27. Zhang, K.; Zhang, L.; Weinreb, R. N. Ophthalmic Drug Discovery: Novel Targets and Mechanisms for Retinal Diseases and Glaucoma. Nat. Rev. Drug Discov. 2012, 11, 541-559.
28. Pierigè, F.; Serafini, S.; Rossi, L.; Magnani, M. Cell-Based Drug Delivery. Adv. Drug Deliv. Rev. 2008, 60, 286-295.
29. Brähler, M.; Georgieva, R.; Buske, N.; Müller, A.; Müller, S.; Pinkernelle, J.; Teichgräber, U.; Voigt, A.; Baümler, H. Magnetite-Loaded Carrier Erythrocytes as Contrast Agents for Magnetic Resonance Imaging. Nano Lett. 2006, 6, 2505-2509.
30. Lee, J.; Choi, J.; Park, J. H.; Kim, M. H.; Hong, D.; Cho, H.; Yang, S. H.; Choi, I. S. Cytoprotective Silica Coating of Individual Mammalian Cells through Bioinspired Silicification. Angew. Chem., Int. Ed. 2014, 53, 8056-8059.
31. Muzykantov, V. R. Drug Delivery by Red Blood Cells: Vascular Carriers Designed by Mother Nature. Expert Opin. Drug Deliv. 2010, 7, 403-427.
32. Yoo, J. W.; Irvine, D. J.; Discher, D. E.; Mitragotri, S. Bio-Inspired, Bioengineered and Biomimetic Drug Delivery Carriers. Nat. Rev. Drug Discov. 2011, 10, 521-535.
33. Ding, X.; Lin, S.-C. S.; Kiraly, B.; Yue, H.; Li, S.; Chiang, I. K.; Shi, J.; Benkovic, S. J.; Huang, T. J. On-Chip Manipulation of Single Microparticles, Cells, and Organisms Using Surface Acoustic Waves. Proc. Natl. Acad. Sci. U.S.A. 2012, 109, 11105-11109.
34. Wang, W.; Li, S.; Mair, L.; Ahmed, S.; Huang, T. J.; Mallouk, T. E. Acoustic Propulsion of Nanorod Motors Inside Living Cells. Angew. Chem., Int. Ed 2014, 126, 3265-3268.
35. Nadal, F.; Lauga, E. Asymmetric Steady Streaming as a Mechanism for Acoustic Propulsion of Rigid Bodies. Phys. Fluids 2014, 26, 082001.
36. Venugopalan, P. L.; Sai, R.; Chandorkar, Y.; Basu, B.; Shivashankar, S.; Ghosh, A. Conformal Cytocompatible Ferrite Coatings Facilitate the Realization of a Nanovoyager in Human Blood. Nano Lett. 2014, 14, 1968-1975.
37. Kolesnikova, T. A.; Skirtach, A. G.; Möhwald, H. Red Blood Cells and Polyelectrolyte Multilayer Capsules: Natural Carriers versus Polymer-Based Drug Delivery Vehicles. Expert Opin. Drug Deliv. 2013, 10, 47-58.
38. Delcea, M.; Sternberg, N.; Yashchenok, A. M.; Georgieva, R.; Baümler, H.; Möhwald, H.; Skirtach, A. G. Nanoplasmonics for Dual-Molecule Release through Nanopores in the Membrane of Red Blood Cells. ACS Nano 2012, 6, 4169-4180.
39. Zhang, E.; Kircher, M. F.; Koch, M.; Eliasson, L.; Goldberg, S. N.; Renström, E. Dynamic Magnetic Fields Remote-Control Apoptosis via Nanoparticle Rotation. ACS Nano 2014, 8, 3192-3201.
40. Valberg, P. A.; Feldman, H. A. Magnetic Particle Motions within Living Cells. Measurement of Cytoplasmic Viscosity and Motile Activity. Biophys J. 1987, 52, 551-561.
41. Wilhelm, C.; Billotey, C.; Roger, J.; Pons, J. N.; Bacri, J. C.; Gazeau, F., Intracellular uptake of Anionic Superparamagnetic Nanoparticles as a Function of Their Surface Coating. Biomaterials 2003, 24, 1001-1011.

42. Gao, W.; Sattayasamitsathit, S.; Orozco, J.; Wang, J. Efficient Bubble Propulsion of Polymer-Based Microengines in Real-Life Environments. Nanoscale 2013, 5, 8909-8914.
43. Hu, C. M. J.; Zhang, L.; Aryal, S.; Cheung, C.; Fang, R. H.; Zhang, L. Erythrocyte Membrane-Camouflaged Polymeric Nanoparticles as a Biomimetic Delivery Platform. Proc. Natl. Acad. Sci. U.S.A. 2011, 108, 10980-10985.
44. Hu, C. M. J.; Fang, R. H.; Zhang, L. Erythrocyte-Inspired Delivery Systems. Adv. Healthcare Mater. 2012, 1, 537-547.
45. Fang, R. H.; Hu, C. M. J.; Zhang, L. Nanoparticles Disguised as Red Blood Cells to Evade the Immune System. Expert Opin. Biol. Ther. 2012, 12, 385-389.
46. Wang, C.; Sun, X.; Cheng, L.; Yin, S.; Yang, G.; Li, Y.; Liu, Z. Multifunctional Theranostic Red Blood Cells for Magnetic-Field-Enhanced in Vivo Combination Therapy of Cancer. Adv. Mater. 2014, 26, 4794-4802.
47. Lee, D.; Cohen, R. E.; Rubner, M. F. Heterostructured Magnetic Nanotubes. Langmuir 2006, 23, 123-129.
48. Xu, T.; Soto, F.; Gao, W.; Garcia-Gradilla, V.; Li, J.; Zhang, X.; Wang, J. Ultrasound-Modulated Bubble Propulsion of Chemically Powered Microengines. J. Am. Chem. Soc. 2014, 136, 8552-855547.
49. Garcia-Gradilla, V.; Orozco, J.; Sattayasamitsathit, S.; Soto, F.; Kuralay, F.; Pourazary, A.; Katzenberg, A.; Gao, W.; Shen, Y.; Wang, J. Functionalized Ultrasound-Propelled Magnetically Guided Nanomotors: Toward Practical Biomedical Applications. ACS Nano 2013, 7, 9232-9240.
50. S. Sanchez, L. Soler and J. Katuri, Angew. Chem., Int. Ed., 2015, 54, 1414.
51. J. Wang, ACS Nano, 2009, 3, 4.
52. W. Wang, W. Duan, S. Ahmed, T. E. Mallouk and A. Sen, Nano Today, 2013, 8, 531.
53. J. Wang, Nanomachines: Fundamentals and Applications, Wiley-VCH, Weinheim, Germany, 2013, ISBN 978-3-52733120-8.
54. Y. Mei, A. A. Solovev, S. Sanchez and O. G. Schmidt, Chem. Soc. Rev., 2011, 40, 2109.
55. M. Pumera, Nanoscale, 2010, 2, 1643.
56. K. Kagan, M. J. Benchimol, J. C. Claussen, E. Chuluun-Erdene, S. Esener and J. Wang, Angew. Chem., Int. Ed., 2012, 51, 7519.
57. W. Gao, S. Sattayasamitsathit, J. Orozco and J. Wang, J. Am. Chem. Soc., 2011, 133, 11862.
58. W. Gao, R. Dong, S. Thamphiwatana, J. Li, W. Gao, L. Zhang and J. Wang, ACS Nano, 2015, 9, 117.
A. Servant, F. Qiu, M. Mazza, K. Kostarelos and B. J. Nelson, Adv. Mater., 2015, 27, 2981.
60. Z. Wu, X. Lin, X. Zou, J. Sun and Q. He, ACS Appl. Mater. Interfaces, 2015, 7, 250.
61. J. Wang and W. Gao, ACS Nano, 2012, 6, 5745.
62. D. Kagan, R. Laocharoensuk, M. Zimmerman, C. Clawson, S. Balasubramanian, D. Kang, D. Bishop, S. Sattayasamitsathit, L. Zhang and J. Wang, Small, 2010, 6, 2741.
63. X. Ma, K. Hahn and S. Sanchez, J. Am. Chem. Soc., 2015, 137, 4976.
64. W. Gao, D. Kagan, O. S. Pak, C. Clawson, S. Campuzano, E. Chuluun-Erdene, E. Shipton, E. E. Fullerton, L. Zhang, E. Lauga and J. Wang, Small, 2012, 8, 460.
65. W. Gao and J. Wang, Nanoscale, 2014, 6, 10486.
66. S. Sanchez, A. A. Solovev, S. Schulze and O. G. Schmidt, Chem. Comm., 2011, 47, 698.
67. A. A. Solovev, W. Xi, D. H. Gracias, S. M. Harazim, C. Deneke, S. Sanchez and O. G. Schmidt, ACS Nano, 2012, 6, 1751.
68. S. Balasubramanian, D. Kagan, C.-M. Jack Hu, S. Campuzano, M. J. Lobo-Castanon, N. Lim, D. Y. Kang, M. Zimmerman, L. Zhang and J. Wang, Angew. Chem., Int. Ed., 2011, 50, 4161.
69. Z. Wu, T. Li, J. Li, W. Gao, T. Xu, C. Christianson, W. Gao, M. Galarnyk, Q. He, L. Zhang and J. Wang, ACS Nano, 2014, 8, 12041.
70. Z. Guanjia, M. Viehrig and M. Pumera, Lab Chip, 2013, 13, 1930.
71. C.-M. J. Hu, R. H. Fang, B. T. Luk and L. Zhang, Nat. Nanotechnol., 2013, 8, 933.
72. C.-M. J. Hu, R. H. Fang, J. Copp, B. T. Luk and L. Zhang, Nat. Nanotechnol., 2013, 8, 336.
73. E. Chambers and S. Mitragotri, Exp. Biol. Med., 2007, 232, 958.
74. M. Hamidi and H. Tajerzadeh, Drug Delivery, 2003, 10, 9.
75. Y. Lee, S. Y. Park, C. Kim and T. G. Park, J. Controlled Release, 2009, 135, 89.
76. C. Wang, X. Sun, L. Cheng, S. Yin, G. Yang, Y. Li and Z. Liu, Adv. Mater., 2014, 26, 4794.
77. M. Delcea, N. Sternberg, A. M. Yashchenok, R. Georgieva, H. Baumler, H. Mohwald and A. G. Skirtach, ACS Nano, 2012, 6, 4169.
78. K. J. Rao, F. Li, L. Meng, H. Zheng, F. Cai and W. Wang, Small, 2015, 11, 2836.
79. P. A. Valberg and H. A. Feldman, Biophys. J., 1987, 52, 551.
80. W. Wang, L. A. Castro, M. Hoyos and T. E. Mallouk, ACS Nano, 2012, 6, 6122.
81. V. Garcia-Gradilla, J. Orozco, S. Sattayasamitsathit, F. Soto, F. Kuralay, A. Pourazary, A. A. Katzenberg, W. Gao, Y. Shen and J. Wang, ACS Nano, 2013, 7, 9232.
82. T. Xu, F. Soto, W. Gao, R. Dong, V. Garcia-Gradilla, E. Magaña, X. Zhang and J. Wang, J. Am. Chem. Soc., 2015, 137, 2163.
83. B. Esteban-Fernández de Avila, A. Martin, F. Soto, M. A. Lopez-Ramirez, S. Campuzano, G. M. Vásquez-Machado, W. Gao, L. Zhang and J. Wang, ACS Nano, 2015, DOI: 10.1021/acsnano.5b02807.

What is claimed is:

1. A method for controlling movement of a red blood cell micromotor comprising:
    selectively exposing a red blood cell having a plurality of magnetic particles contained therein to an external magnetic field; and
    propelling the red blood cell in a controlled manner using acoustics, wherein the external magnetic field influences and guides movement of the red blood cell.

2. The method of claim 1, wherein the acoustics are ultrasound.

3. The method of claim 1, wherein the magnetic particles have a diameter of from about 1 nm to less than 100 nm.

4. The method of claim 1, wherein the magnetic particles have a diameter of from about 1 nm to about 20 nm.

5. A method for diagnostic imaging using a red blood cell micromotor comprising:
    selectively exposing a red blood cell having a plurality of magnetic particles and an imaging agent contained therein to an external magnetic field;
    propelling the red blood cell in a controlled manner using acoustics, wherein the external magnetic field influences and guides movement of the red blood cell; and
    imaging the imaging agent.

6. The method of claim 5, wherein the acoustics are ultrasound.

7. The method of claim 5, wherein the magnetic particles have a diameter of from about 1 nm to less than 100 nm.

8. The method of claim 5, wherein the magnetic particles have a diameter of from about 1 nm to about 20 nm.

9. A method of treatment using a red blood cell micromotor comprising:
   selectively exposing a red blood cell having a plurality of magnetic particles and a therapeutic agent contained therein to an external magnetic field and an acoustical field to propel the red blood cell; and
   moving the red blood cell in a controlled manner using the acoustical field to a site in need of therapeutic treatment.

10. The method of claim 9, wherein the acoustical field is ultrasound.

11. The method of claim 9, wherein the magnetic particles have a diameter of from about 1 nm to less than 100 nm.

12. The method of claim 9, wherein the magnetic particles have a diameter of from about 1 nm to about 20 nm.

* * * * *